(12) United States Patent
Kiehne (10) Patent No.: US 7,147,621 B2
(45) Date of Patent: Dec. 12, 2006

(54) SINGLE USE SYRINGE

(75) Inventor: Bruce Leigh Kiehne, Springwood (AU)

(73) Assignee: Occupational & Medical Innovations Ltd., Slacks Creek (AU)

( * ) Notice: Subject to any disclaimer, the term of this patent is extended or adjusted under 35 U.S.C. 154(b) by 0 days.

(21) Appl. No.: 10/474,516

(22) PCT Filed: May 17, 2002

(86) PCT No.: PCT/AU02/00612

§ 371 (c)(1),
(2), (4) Date: Oct. 22, 2003

(87) PCT Pub. No.: WO02/094355

PCT Pub. Date: Nov. 28, 2002

(65) Prior Publication Data

US 2004/0116857 A1 Jun. 17, 2004

(30) Foreign Application Priority Data

May 22, 2001 (AU) .................................... PR5169

(51) Int. Cl.
*A61M 5/00* (2006.01)
*A61M 5/32* (2006.01)

(52) U.S. Cl. ........................................ 604/110; 604/192
(58) Field of Classification Search ................ 604/110, 604/195, 198, 197, 218, 222, 192
See application file for complete search history.

(56) References Cited

U.S. PATENT DOCUMENTS 6,010,486 A    1/2000   Carter et al.

FOREIGN PATENT DOCUMENTS

| ES | 2 147 118 | 2/1998 |
|----|-----------|--------|
| WO | WO 96/35453 | 11/1986 |
| WO | WO 94/04207 | 3/1994 |
| WO | WO 01/62320 | 2/2000 |
| WO | WO 00/64515 | 11/2000 |

*Primary Examiner*—Michael J. Hayes
(74) *Attorney, Agent, or Firm*—Hoffman, Wasson & Gitler, P.C.

(57) ABSTRACT

A single use syringe uses a "pinching" action between a specially designed plunger and a specially designed needle holder to shoot the needle back into the syringe body upon completion of the piston stroke. The needle is not biased by a helical spring and the syringe remains in an unbiased condition until the plunger is pushed against the needle holder that creates the pinching action to shoot the needle back into the syringe body.

12 Claims, 7 Drawing Sheets

SINGLE USE SYRINGE

FIELD OF THE INVENTION

This invention relates to a single use syringe of the type that has a needle that shoots back into the syringe body after use. The invention is particularly directed to various improvements to this type of syringe, including improvements to the shoot back mechanism. The shoot back mechanism need not require a helical spring, and the bias required to shoot back the syringe needle can be created by a combination of a specially configured plunger head pushing up against a specially configured needle holder. Thus, the bias required to shoot back the needle is formed or created just before use (i.e. when the plunger is fully pushed into the barrel), which means that when the plunger is in the retracted position, the needle is not biased. Conventional shoot back needle assemblies typically have the needle permanently biased.

BACKGROUND ART

Single use syringes are required to reduce the risk of infection caused by needle sharing. Many types of single use syringes are known.

One type of syringe that shoots the needle back into the syringe body is extremely complicated and has up to 16 parts that must be assembled to form the finished syringe. This known syringe is also restricted to volumes of larger than 3 ml as the various parts cannot be made to fit smaller syringes.

Another disadvantage with known syringes of this type is the inability to easily and readily injection mould the various components. For instance, a syringe having a shoot back needle is known where a spring biased needle is held in place by a rupturable restraining means which is moulded as part of the internal wall of the syringe barrel. In practice, it is found that such a barrel is extremely difficult to mould and is virtually impossible to injection mould. Thus, this type of syringe cannot be manufactured cheaply.

Another type of safety syringe having a spring-mounted needle that shoots back into the plunger stem has a needle held in place by a deformable base. The deformable base has a constricted passageway which grips a peculiarly designed needle that has inter alia a circular flange attached to it. The deformable member is pushed forward by the plunger and in doing so, it is pushed forwardly into an area of larger cross-section which allows the deformable member to expand which in turn allows the needle to pass through the passageway in the deformable member and to shoot back into the plunger stem. One disadvantage with this design is that a standard needle cannot be used.

Safety syringes having shoot back needles are also known where the needle is not biased by a spring. Instead, a vacuum is provided in the barrel to suck the needle back into the plunger stem. This type of syringe is of course fairly limited in use to circumstances where suction can be provided.

Another type of syringe that does not have a biased needle instead has a plunger stem provided with a helical spring such that the plunger stem is biased to retract. The plunger stem is pushed along the barrel and against the bias of the spring. When the front of the plunger stem strikes the rear of the needle, it locks against the needle. Release of the plunger stem will then cause the spring to pull the plunger stem back along the barrel thereby retracting the needle.

It is known to provide single use syringes where the needle is spring biased and is held in place by a cuttable member. In order to ensure that the member is properly cut thereby releasing the needle, a two-part cutting action is usually required. In the two-part cutting action, the plunger typically has a forward cutting edge and the front of the needle also has some form of cutting edge and a double cutting action is required to ensure that the cuttable member is property cut to release the needle. It is found that attempting to cut a cuttable member to release a spring-biased needle is not always reliable and does not always work.

Another type of known single use syringe has a base member that grips an enlargement on the needle. The plunger pushes the base member forwardly, which further compresses a spring that is around the needle. The pushing action releases the grip between the base member and the enlargement on the needle. This allows the needle containing the enlargement to be shot back into the plunger while leaving the spring behind. The spring is initially compressed partially but then becomes compressed fully as the plunger forces the base member forwardly. This arrangement requires a needle having a special design (containing an enlargement), which means that conventional needles cannot be used.

Another type of syringe has a plunger seal which moves on the plunger and where the plunger seal slides rearwardly along a bearing surface in response to a force being applied to the seal that is in excess of the operational force of the syringe. This arrangement begins the retraction sequence of the needle. With this arrangement, a specially designed plunger seal is required which moves relative to the plunger. Conventional plungers have a plunger seal that is fixed to the plunger.

Another type of syringe has a shoot back arrangement consisting of two parts which slide relative to each other to release the needle. The two parts consist of an outer part and an inner part. The inner part holds the needle and is biased by a helical spring. The two parts are held together by frictional engagement to each other. A plunger progressively pushes the outer part forwardly thereby progressively reducing the amount of frictional engagement between the outer part and the inner part until such time that the bias of the spring is sufficient to shoot the inner part away from frictional engagement with the outer part. This arrangement requires a sliding frictional grip to hold the two-part together which is considered quite risky and requires careful manufacture.

Another arrangement uses a needle holder having an elongate body portion in front and a head end in back and providing a spring under the head end that circumscribes the needle holder. The use of an elongate body in a needle holder makes this arrangement difficult for use in small and confined spaces.

Therefore, in summary, the known single use syringes all use some form of spring, and typically a helical spring to shoot back the needle. In each of these versions, the needle is biased to shoot back into the syringe body, and needs to be held in place to prevent this from occurring. However, there does not appear to be a version where the needle is not always biased, or is not biased at all during the injection cycle. The versions that use vacuum to suck back the needle have too many disadvantages to make them commercially versatile and acceptable.

Another disadvantage with many existing single use syringes, is that the mechanism required to shoot back the needle often has a portion protruding into the syringe barrel, and can result in incomplete expulsion of the liquid from the barrel and through the needle. In other words, many existing single use syringes have a "dead space" where the syringe fluid can collect and where the fluid will not be properly expelled from the syringe. This can result in incomplete or erroneous levels of fluid being injected into a person. The present invention may also include means to reduce "dead space" in the syringe barrel.

Another disadvantage with some of the spring biased shoot back needles, is that in practice, it is possible to reassemble the mechanism which means that the syringe and needle can be reused. Clearly, a single use syringe should be manufactured in such a manner that it would be impossible to reuse the syringe. Therefore, there would be an advantage in having some form of "destructive mechanism" which would render the syringe unable to be reused.

Another disadvantage with single use syringes, and perhaps also with other types of syringes that contain needles is the risk of needle stick when removing the cap that protects the needle. Typically, the cap has some form of releasable press fit arrangement, and the cap needs to be gripped by person's fingers and pulled off the syringe to expose the needle. Therefore, there would be an advantage in having some form of needle cap that could be removed in a safer manner to reduce the incidence of needle stick.

OBJECT OF THE INVENTION

It is an object of the invention to provide a single use syringe which has a needle shoot back mechanism, and optionally other features which may overcome the above-mentioned disadvantages or provide the public with a useful or commercial choice.

It is a preferable object of the invention to provide a single use syringe that does not have a needle that is biased by a helical spring during the injection stroke.

In one form, the invention resides in a single use syringe that has:

a syringe body which has an open rear end, and a front end formed with an opening, a needle assembly which comprises a needle which has an outer end and an inner end, and a needle holder which is attached to the inner end of the needle, the needle holder having a body portion which has an inner end and an outer end, the inner end of the body portion extending into the syringe body and having a tapered face, the outer end of the body portion extending into the opening in the front end of the syringe, and being sealingly engaged thereto, a plunger moveable along the syringe body, the plunger having a plunger body and a plunger head, the plunger head being formed with a concave portion which is adapted to extend about at least portion of the inner end of the body portion when the plunger head is pushed against the inner portion, the plunger additionally having sealing means to seal the plunger against the inside wall of the syringe body, the sealing means being attached to the plunger via a hinge means, a forward part of the plunger adapted for compressive engagement with the needle holder to provide a propelling force and for freeing the outer end of the body portion from sealing engagement with the opening, thereby allowing the needle holder to be shot back into the syringe body.

The single use syringe can come in various shapes sizes and volumes. The syringe body is typically cylindrical, hollow, and has an open rear end through which the plunger can pass, and a front end that is closed apart from a small opening through which the needle can pass. A luer tip need not be provided on the syringe that is the subject of this invention. The opening typically extends approximately centrally through the otherwise closed front end of the syringe.

The needle assembly may comprise a needle holder and a needle. The needle can be a conventional needle, which is an advantage of the invention in that a specially designed needle is not required. The needle holder can be made of plastic, and is typically designed to fit inside the syringe body. The needle holder may be somewhat arrow shaped and has an inner end and an outer end, the outer end typically at least partially passing through the opening in the front of the syringe body and typically being sealing the engaged thereto. Suitably, the needle holder is held in place by the sealing engagement of the outer end in the opening. As a helical biasing spring is not essential, there is no need for the needle holder to be held extremely strongly or tightly in place, as the needle holder is not continuously biased.

The plunger has a plunger body and a plunger head. The plunger body is typically hollow to provide a space for the needle when the needle is shot back into the syringe body. The plunger body need not be entirely hollow, and may have a passageway to accommodate the needle, or some other form of recess or groove to accommodate the needle.

The plunger head is formed with a concave portion that typically extends into the plunger body. The concave portion may be formed integrally with the plunger head. As the concave portion is designed to split and break, the concave portion typically has a wall thickness that is less than the wall thickness of the remainder of the plunger body. Lines of weakness may be provided in the concave portion to facilitate controlled splitting or breaking. The concave portion typically has a profile to substantially conform to the profile of the inner end of the needle holder to reduce or eliminate any "dead space" when the plunger is pushed forwardly against the end of the syringe barrel.

A sealing means is provided to seal the plunger against the inside wall of the syringe barrel as the plunger is moved forwardly. The sealing means may comprise an annular flange. The sealing means may extend forwardly and radially outwardly from the remainder of the plunger. The sealing means may be formed integrally with the plunger body.

A hinge means may be provided between the sealing means and the plunger body. The hinge means may comprise a portion of reduced thickness. The hinge means may allow the sealing means and the plunger body to move towards or away from each other.

BRIEF DESCRIPTION OF THE DRAWINGS

An embodiment of the invention will be described with reference to the following drawings.

BEST MODE

Figure 1:
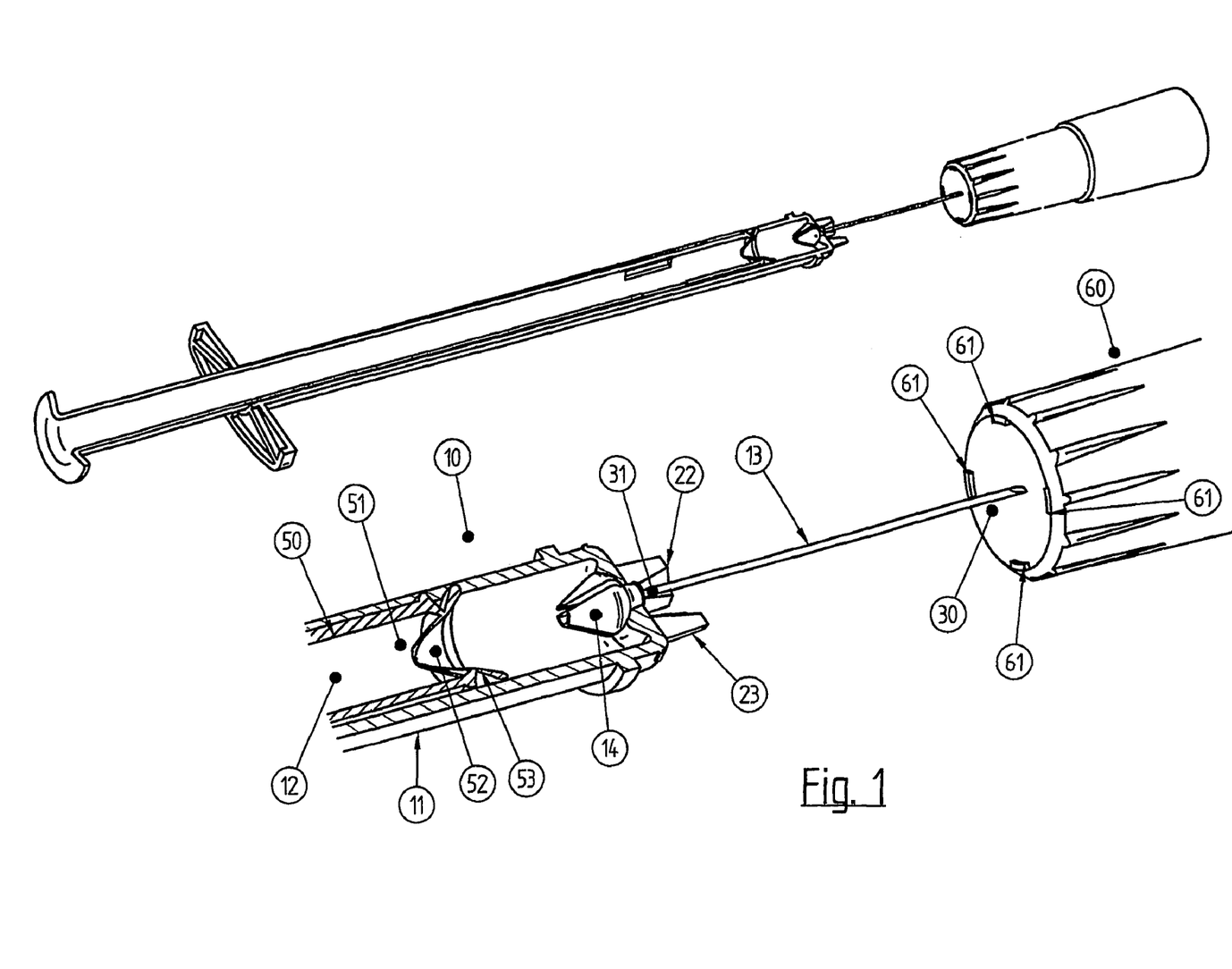
FIG. 1. Illustrates a section view of a single use syringe according to an embodiment of the invention where the plunger is beginning its forward stroke towards the end of the syringe.

Referring to the drawings, and initially to FIG. 1, there is illustrated a single use syringe 10 which has a syringe body 11, a plunger 12 which slides along the syringe body, a needle 13 which can be of conventional design, and a needle holder 14.

Syringe 10 has an elongate syringe body as is known. The syringe body has a forward end portion 15 and a rearward end 16. The rearward end is open to allow the plunger to pass into and out of the syringe body. A radially extending flange 17 is attached to the rearward end 16 of the syringe body, as is known.

The syringe body differs from conventional syringes in the forward end portion 15. This is best illustrated in FIGS. 2–5. The forward end portion has a radially extending circumferential rib which functions to facilitate removal of the integrally formed cap 60 as will be described in greater detail below.

The forward end portion 15 has a front face 20. Front face 20 is provided with a more or less central opening 21 which is typically circular and has a diameter of between 0.5–5 mm. Extending outwardly from front face 20 are four bosses (only two 22, 23 being shown). Bosses 22, 23 have several functions. One function is to strengthen the front face 20 of the forward end portion such that the front face does not split during the compressive forces which are applied when the plunger is pushed hard up against the inside of the front face. Another function is to act as a guide when the cap 60 is removed from the syringe body, that is, to prevent the cap from striking the base of the needle as the cap is removed. Another function of the bosses is to protect the base area of the needle. Another function of the bosses is to provide a support when the needle is pushed into a vein (it being appreciated that most needle insertions are conducted with the needle at only a slight angle to the persons body such that the needle can be inserted into a vein). The bosses assist in supporting the syringe at the correct angle. The bosses are arranged such that the needle 13 passes between the bosses.

The front face 20 is formed integrally with the remainder of the syringe body. The wall thickness of front face 20 is not uniform, and the wall has an inwardly extending bulbous part 24 part of which defines the wall of opening 21. Bulbous part 24 has a rather complex geometry and comprises a first portion 25 which forms the wall of opening 21, a second portion 26 which has a land portion 27 which tapers outwardly, and a third portion 28 which has a land portion 29 which can be seen as a return portion. The reason for this geometry will be explained below, but forms part of the shoot back mechanism.

Needle 13 can be of conventional design, which is an advantage over some other single use syringes that require a specially designed needle. The needle has an outer end 30, which is typically pointed, and an inner end 31. A needle holder 14 is attached to the inner end 31 of needle 13.

Needle holder 14 shoots back with the attached needle 13 during the shoot back cycle. Needle holder 14 is manufactured from plastics material. The needle holder has a body portion 34. Body portion 34 has an inner end 35 that extends into the syringe body, and an outer end 36 that fits into opening 21 on the front face of the syringe body. The outer end 36 terminates with a small peripheral lip 37 that extends over the front face of the syringe body to facilitate holding the needle holder in place. The needle holder 14 is held in place inter alia by being pressed fitted into opening 21. Thus, the needle holder 14 seals opening 21. Needle holder 14 has a longitudinal passageway 38 through which the needle 13 passes.

Figure 10:
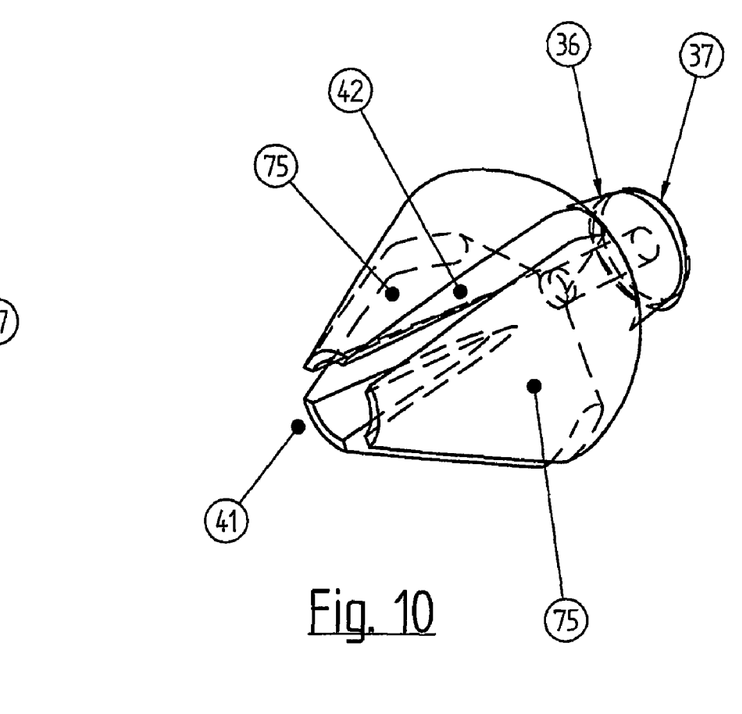
FIG. 10. Illustrates the needle holder from the front.

The inner end 35 of needle holder 14 has a tapered front face 39 and this front face is substantially in the form of a cone. The front face has at least one recess 40 extending there through, the recess being open at the front 41 of front face 39, and also at each side 42 of the front face 39. The reason for this will be described below. The rear of recess 40 communicates with passageway 38 through which needle 13 passes. The front face can be seen to have a number of fingers 75 (see FIG. 10) (typically between 2–4) which extend rearwardly into the syringe barrel from a common base, the base being the portion of maximum width or circumference 43. The fingers are spaced apart to define recess 40.

The geometry of needle holder 14 is such that as well as having the tapered front face 39, the inner end 35 has a portion of maximum width or circumference 43 (indicated by the imaginary line), and behind this portion, is a substantially cylindrical land portion 44 which tapers downwardly towards the substantially cylindrical outer end 36. This geometry forms part of the shoot back mechanism.

Referring now to the plunger, plunger 12, has a plunger body 50 which is typically tubular, is hollow, and is formed from sufficiently rigid plastics material. The forward end of plunger body 50 has a plunger head 51 of special design. Plunger head 51 has a complex shape.

The plunger head comprises a concave portion 52 that extends over the otherwise open forward end of plunger body 50. The concave portion is sufficiently dimensionally stable to maintain its concave shape during the injection stroke. The concave portion may be formed from the same material as plunger body 50, and may be formed integrally with the plunger body, but has a thinner wall thickness than the remainder of the plunger body. The reason for this is that the concave portion is designed to split, break or rupture as part of the shoot back mechanism. This will be described in greater detail below. The concave portion 52 is shaped to complement the shape of the inner end 35 of needle holder 14. Thus, the concave portion may be substantially cone shaped if the inner end 35 of needle holder 14 is also cone shaped.

The plunger head further contains an annular member 53 which functions inter alia as a seal. Annular member 53 can be formed integrally with plunger body 50. The geometry of annular member 53 is best illustrated in figures 2–5. It can be seen that annular member 53 extends from a forward most part of the plunger head, and becomes progressively thicker from where the annular member joins the plunger head to the free end of the annular member that is rounded. The joint 54 of the annular member to the plunger head can be seen as a hinge point.

The operation of the single use syringe will now be described. The syringe can be filled in the usual manner by drawing fluid through needle 13, and retracting the plunger 12. Retraction of the plunger 12 will cause a partial vacuum to be created in the syringe body that will cause fluid to be sucked through the needle. Needle holder 14 is held in place by being frictionally gripped by the wall of opening 21, and by the small peripheral lip 37. Thus, the needle holder 14 is not dislodged during the syringe-filling stroke.

When expelling fluid from the syringe, plunger 12 is pushed forwardly in the usual manner. Needle holder 14 is clearly unable to become dislodged during the forward stroke, as the body of needle holder 14 is much larger than opening 21. Importantly, a spring or any similar mechanism does not bias the needle and the needle holder.

Figure 2:
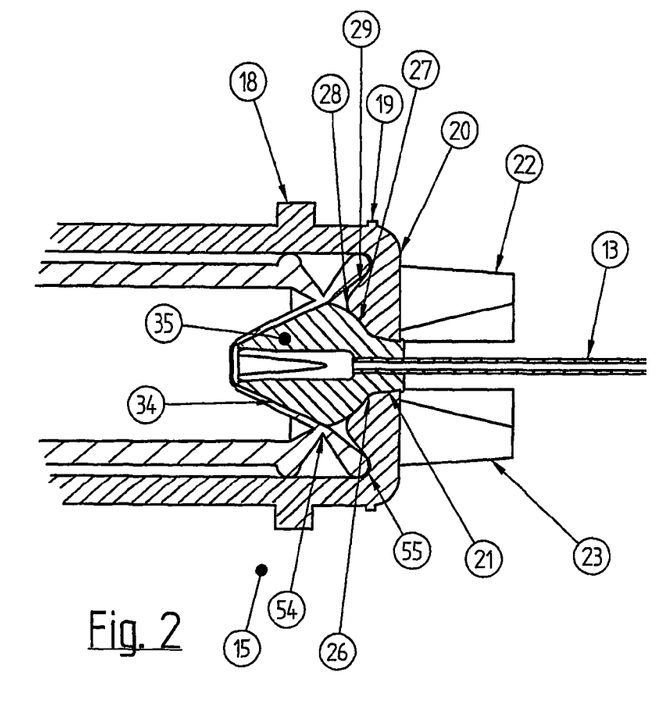
FIG. 2. Illustrates a close-up section view of the forward part of the plunger making contact with the needle holder.

The needle holder and the needle are caused to shoot back into the plunger body by compression forces that come into effect when the plunger is pushed hard against the needle holder. The compression forces are created as follows. Referring initially to FIG. 2, at this position, the plunger has been pushed forwardly and is lightly touching needle holder 14 and the inner end of the front face of the syringe. More specifically, the concave portion 52 is overlying the inner tapered face 35 of needle holder 14, and the rounded end 55 of annular member 53 is positioned in a edge at the front end of the syringe barrel. Also, the hinge join area 54 is positioned at or adjacent the widest portion 43 of the needle holder.

Another advantage of the invention becomes apparent in this position; this is the reduction or almost total elimination of any "dead area" in the syringe barrel. That is, the syringe according to the invention allows almost total, or allows total expulsion of all the fluid withing the syringe. The concave portion 52 substantially overlying inner end 39 achieves this. The recess 40 may have slightly rounded edges which facilitate expulsion of fluid through needle 13 before the recess is sealed by concave portion 52. The rounded edges may be useful to allow the conical tip to compress inwards without stressing.

Figure 3:
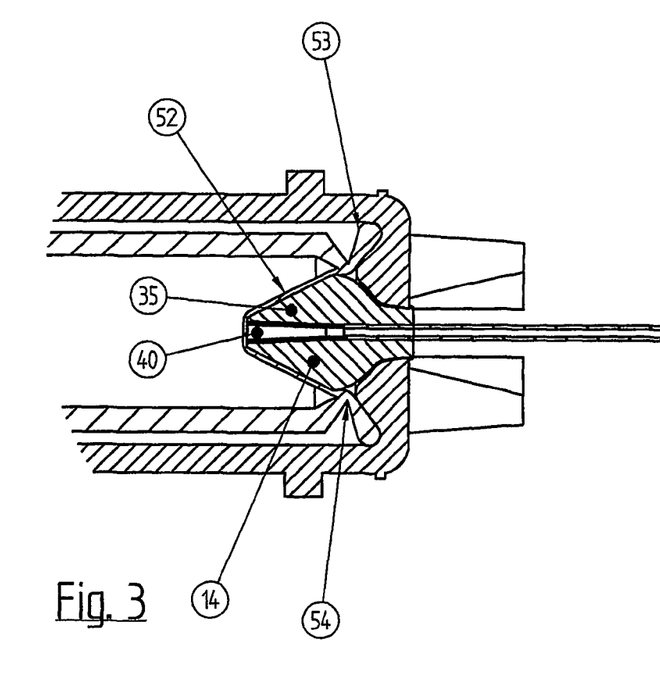
FIG. 3. Illustrates the view of FIG. 2 where the plunger is being pushed further forwardly to provide compression forces about the needle holder.
Figure 4:
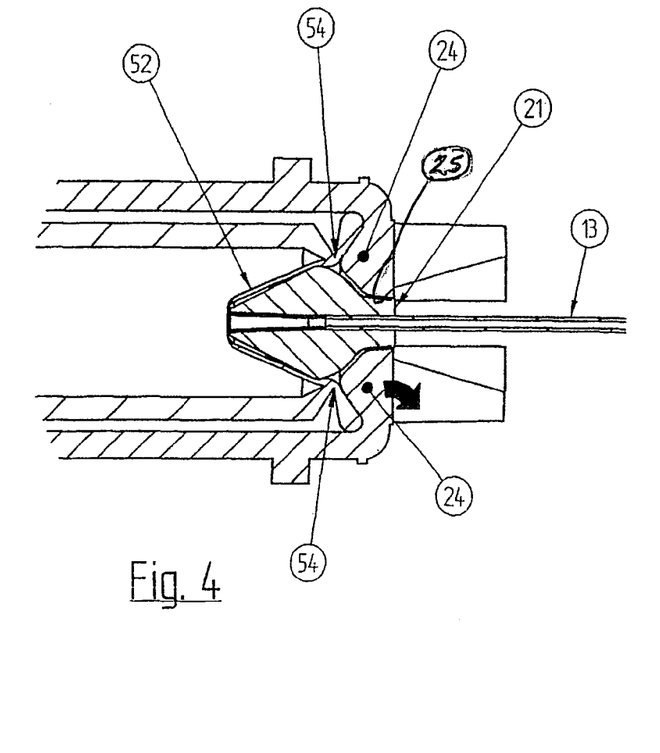
FIG. 4. Illustrates the view of FIG. 3, where plunger is being pushed further forwardly and the needle holder is at the point of being shot back into the plunger body.

At the position illustrated in FIGS. 3 and 4, the plunger is being pushed harder against the front of the syringe barrel. At this stage, compressive forces are created which provides the "spring" or "pushing force" to shoot back the needle. Specifically, at the position illustrated in FIG. 3, the hinge area 54 has now been pushed past the portion of widest diameter 43 on needle holder 14. The concave portion 52 is now being pushed harder against the inner end 35 of the needle holder and is beginning to stretch or weaken. The annular member 53 is being pushed back towards the plunger body about hinge area 54. The hinge area 54 is also beginning to compress the needle holder 14 at or slightly behind portion 43, compression of the needle holder being facilitated by recess 40 that is being squeezed shut. As well, the hinge area 54 is beginning to contact the bulbous part 24. The tip compresses to assist in the splitting of the membrane in the concave portion. The conical section opens up after the hinge area has past the widest section of the needle holder. This further stretches the membrane and applies an additional force in reaction to the inwardly compressive force of hinge 54.

Figure 5:
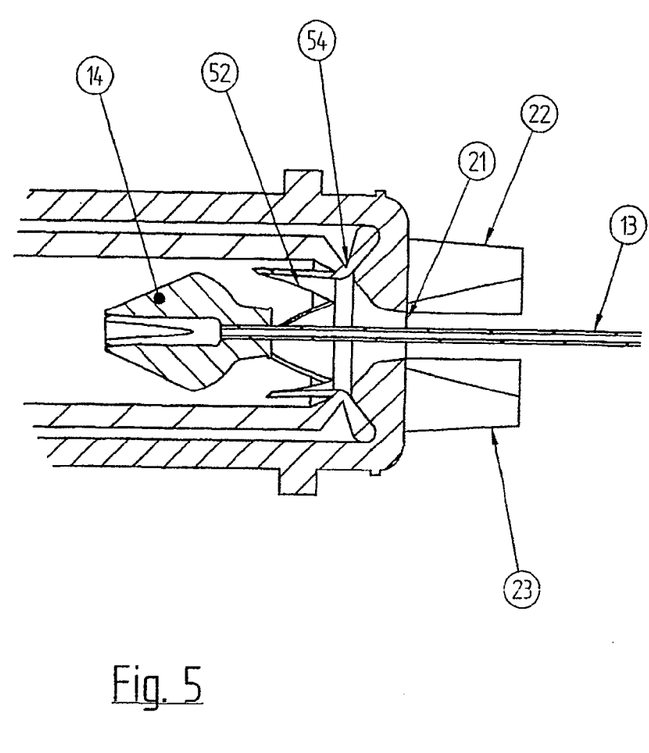
FIG. 5. Illustrates the view of FIG. 4, where the needle holder has been released and the compressive forces are shooting the needle back into the plunger body.
Figure 6:
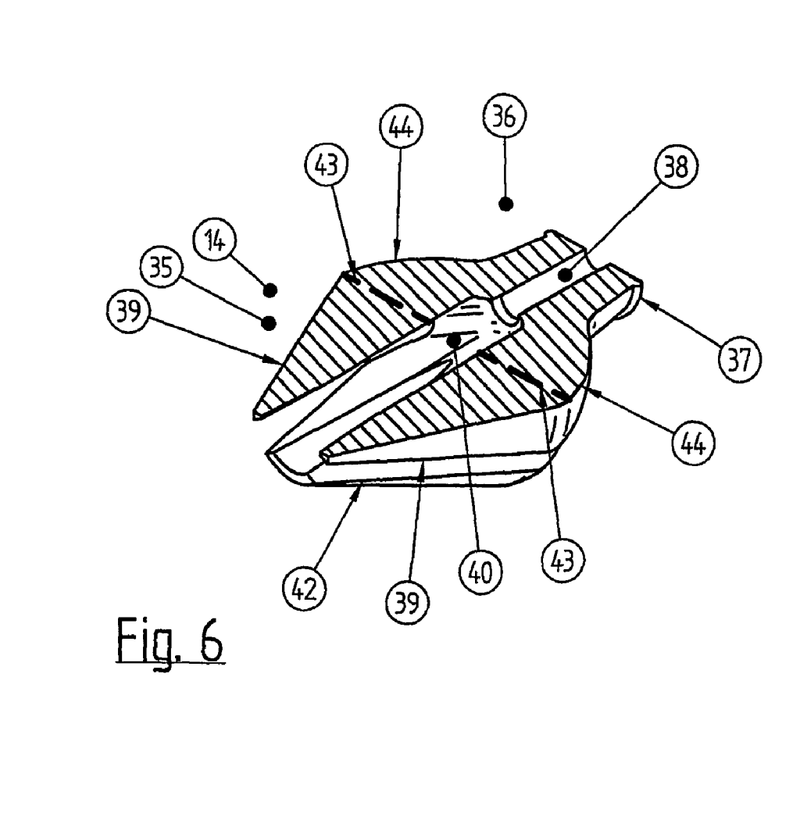
FIG. 6. Illustrates a close up section view of the needle holder.
Figure 7:
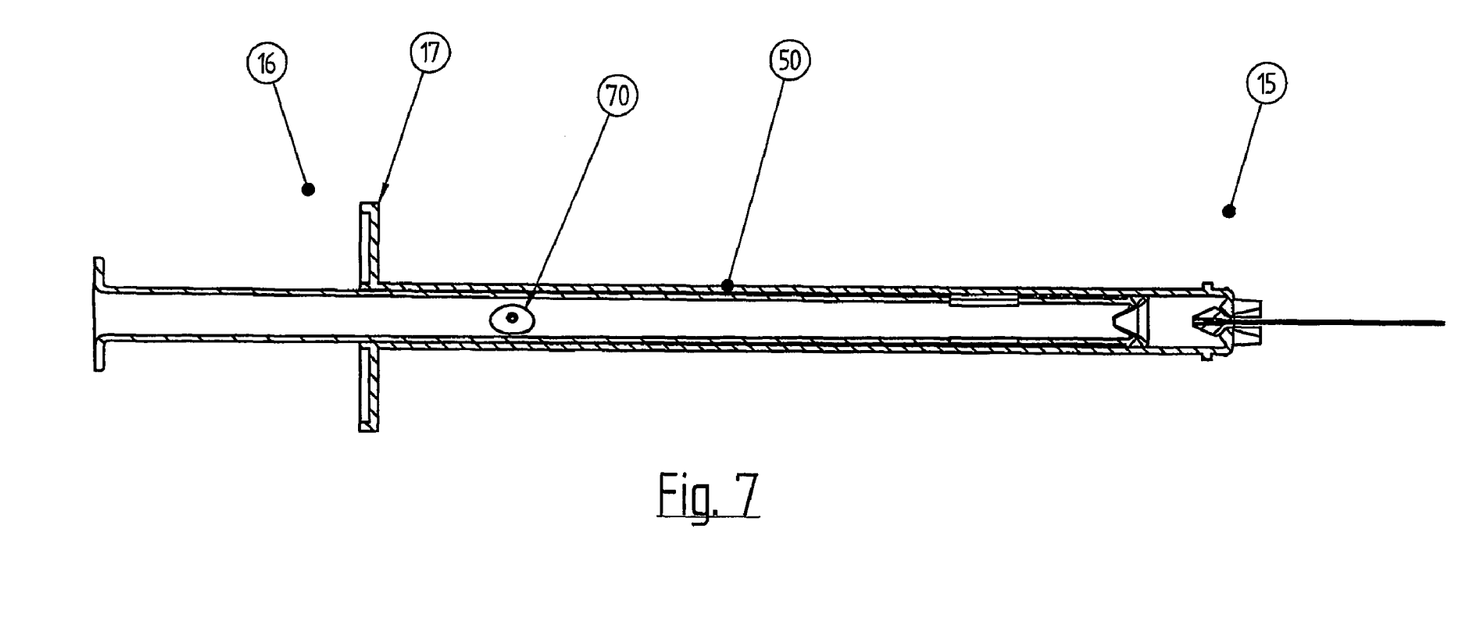
FIG. 7. Illustrates a side view of the syringe.
Figure 11:
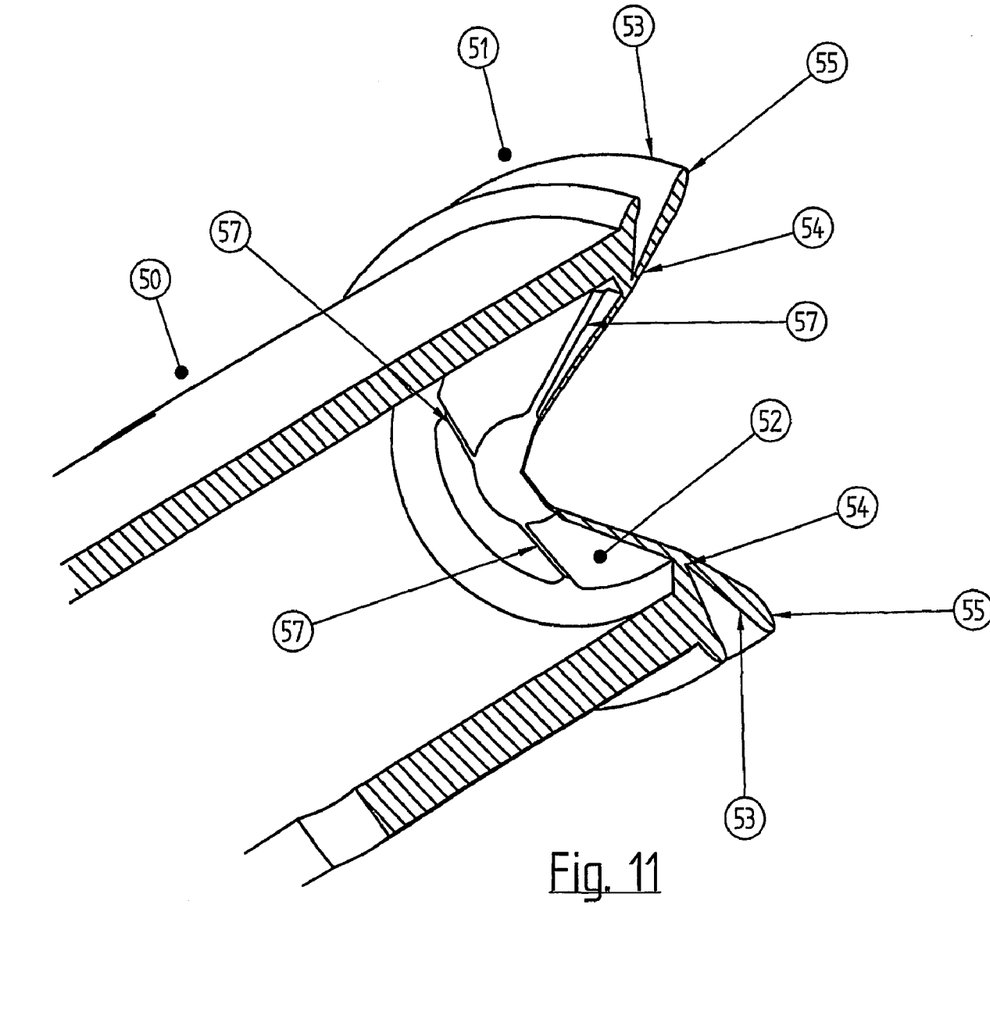
FIG. 11. Illustrates a rear partially cut away view of a forward part of the plunger

At the position illustrated in FIG. 4, the compressive forces are just about sufficient to shoot back the needle and the needle holder. At this position, the hinge area 54 is pushing against bulbous part 24 and is causing the bulbous part 24 to move forwardly, which in turn, causes opening 21 to increase in size. By doing so, the grip between needle holder 14 and the walls of opening 21 is reduced. Continued pushing causes opening 21 to increase to the point that the grip is sufficiently reduced, and the small lip 37 on needle holder 14 can pass through opening 21. Simultaneously with this action, the needle holder is being squeezed or compressed by the plunger, and the main force is slightly in front of portion 43 (that is between portion 43 and bulbous part 24). At this point, concave portion 54 begins to split. To facilitate and control the splitting action, concave portion 54 can be provided with one or more shallow grooves or recesses 57 (see FIG. 11) (which can be seen as lines of weakness or frangible portions) in the wall of concave portion 54. These grooves or recesses will begin to split first and provide a controlled splitting or tearing of concave portion 54. When this occurs, the hollow inside part of the plunger becomes available for the needle and the needle holder to shoot back into the plunger. The compressive action described above, can be seen as a "inching" action behind the widest portion of the needle holder, together with release of the needle holder from frictional engagement with the walls of opening 21. The pinching action will propel the needle holder containing the attached needle back into the plunger body at some speed. Importantly, as the concave portion has split, there is a "destructive" shoot back mechanism that ensure that the syringe cannot be used again. FIG. 5 illustrates the position where the needle holder is being shot back into the plunger body. hot back into the plunger body.

When the needle holder is shot back into the interior of the plunger body, it is held in place by an engagement means 70 which prevents the needle holder from being removed from the plunger body. Various types of engagement means are envisaged including reverse conical split sections in the plunger cavity.

Figures 8, 9:
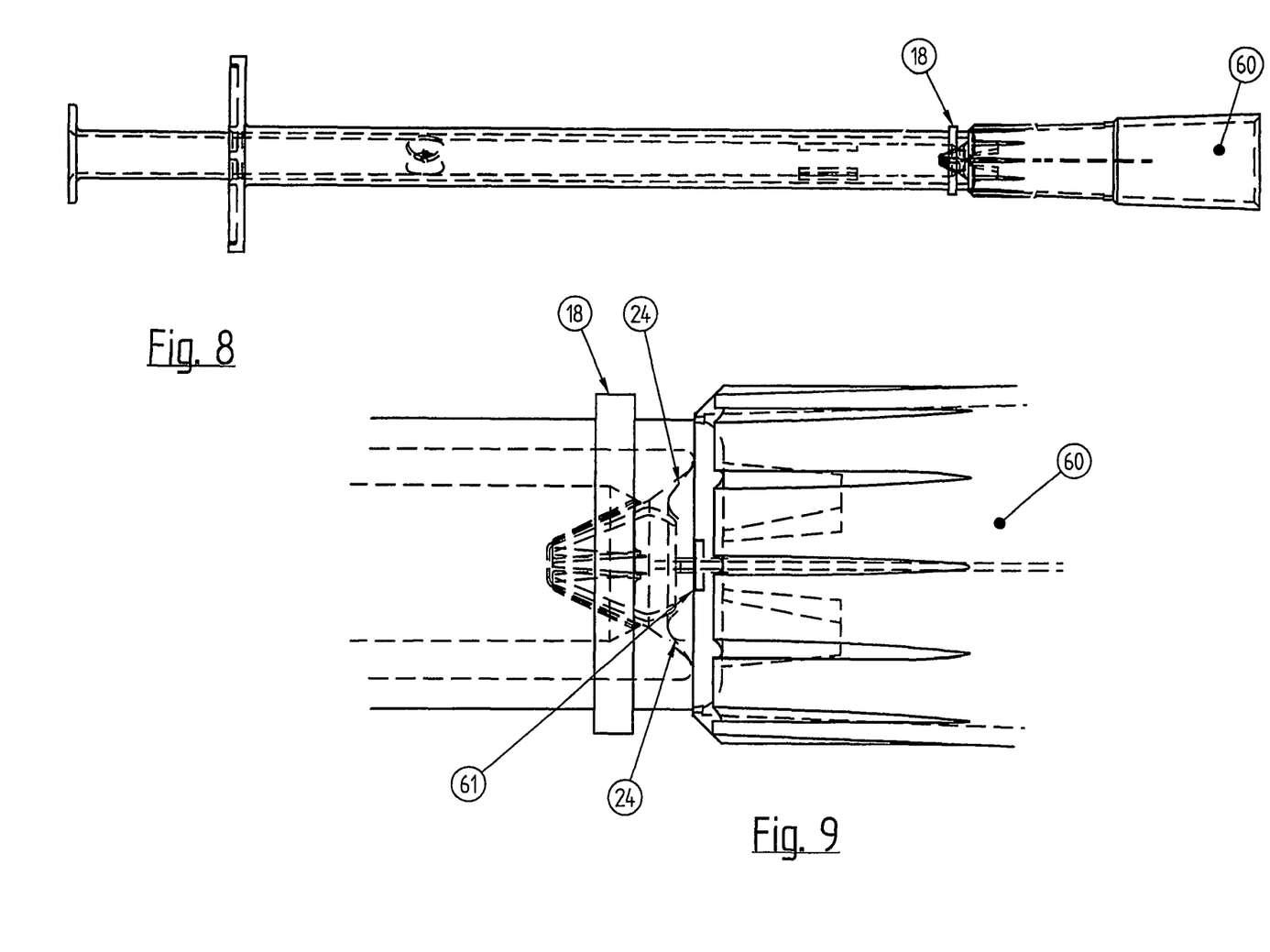
FIG. 8. Illustrates a single use syringe with an integrally formed cap.
FIG. 9. Illustrates a close up view of the attachment of the cap to the syringe body.

Another feature of the invention is in the design of the cap 60. As described above, removing the needle cap from the needle causes a source of needle stick injury. One form of the present invention can reduce or eliminate needle stick injury caused in this manner. In this form of the invention, the needle cap 60 is formed integrally with syringe body 11. Cap 60 is attached to the front of syringe body 11 via a number of frangible portions or tabs 61 best illustrated in FIGS. 1, 8 and 9. During assembly, the needle and needle holder are positioned by feeding them through the rear of syringe body, as cap 60 is formed integrally with the syringe body. In use, and to remove the cap, the syringe containing the integral cap can be held around the syringe body and can be tapped onto a hard surface, with the cap 60 being tapped against the hard surface. This action breaks the frangible portions 61, and cap 60 is then pushed over the front of the syringe body until it abuts against rib 18. This function of rib 18 is to prevent the cap from moving too far along the syringe body. The cap is now loose, and if the syringe is held vertically, the cap will simply drop away from the syringe to expose the needle without a person requiring any touching of the cap. In FIG. 2, reference numeral 19 indicates the attachment points of cap 60 to the syringe body. The length of cap 60 is sufficient to ensure that the tip of needle 13 will not strike the inside end wall of the cap when the cap is against rib 18. In an embodiment, cap 60 is open ended and has a length sufficient to cover the needle, and has a diameter which is small enough to not pose a sharps risk.

Another advantage of an integrally moulded cap is that it can be seen as a very good "tamper evident" cap, as the cap can only be removed by destruction of frangible portions 61 which makes it very easy to see if the cap has been tampered with. Although the cap 60 can be removed as described above, the cap can also be removed by twisting it relative to the syringe body to break frangible portions 61. This opening action does require a person to touch the cap, but it is considered that a twist action is safer than a pull action in order to remove the cap.

The single use syringe according to the embodiment has many advantages. One advantage is that a mechanical spring is not required which reduces assembly of the syringe. By not requiring a mechanical spring, there is no possibility of any spring fatigue. In the embodiment, the forces required to shoot back the needle and the needle holder are provided only when the plunger is pushed against the inside front wall of the syringe body. This means that the parts of the syringe are otherwise in an unstressed state, and the shoot back forces are only supplied when required. Of course, if desired, a supplementary biasing means can be used to assist in propelling the needle and needle holder back into the plunger stem.

It should be appreciated that various changes and modifications can be made to the embodiment described without departing from the spirit and scope of the invention.

What is claimed is:

1. A single use syringe that has:
   a syringe body which has an open rear end, and a front end formed with an opening,
   a needle assembly which comprises a needle which has an outer end and an inner end, and a needle holder which is attached to the inner end of the needle, the needle holder having a body portion which has an inner end and an outer end, the inner end of the body portion extending into the syringe body and having a tapered face, the outer end extending into the opening in the front end of the syringe body, the body portion having a circumferential portion which initially diverges and then converges from the inner end to the outer end, the needle holder being releasably attached adjacent the front end of the syringe body,
   a plunger moveable along the syringe body, the plunger having a plunger body and a plunger head, the plunger head being formed with a concave portion which is adapted to extend about at least a portion of the inner end of the body portion of the needle holder when the plunger head is pushed against the inner portion, the plunger having sealing means extending in front of the plunger head to seal the plunger against the inside wall of the syringe body, the sealing means being attached to the plunger via a hinge portion, the sealing means pushing against the front of the syringe body when the plunger is pushed fully forwardly and causing the opening in the front end of the syringe body to enlarge thereby releasing the needle holder, the forward part of the plunger adapted for compressive engagement with the converging portion on the needle holder to provide a propelling force to shoot the needle holder back into the plunger body.

2. The syringe as claimed in claim 1, wherein the plunger body is provided with a passageway to accommodate the needle.

3. The syringe as claimed in claim 1, wherein the concave portion on the plunger head is adapted to break when the plunger head is pushed against the body portion of the needle holder.

4. The syringe as claimed in claim 3, wherein the concave portion has a profile which substantially conforms to the profile of the inner end of the needle holder to reduce any dead space when the plunger is pushed forwardly against the end of the syringe barrel.

5. The syringe as claimed in claim 4, wherein the sealing means comprises an annular member which extends forwardly and radially outwardly from the remainder of the plunger.

6. The syringe as claimed in claim 5, wherein the hinge portion allows the sealing means and plunger body to move towards or away from each other.

7. The syringe as claimed in claim 1 including a cap.

8. The syringe as claimed in claim 7, wherein the cap is attached to the syringe body via at least one frangible portion.

9. The syringe as claimed in claim 8, wherein the cap is formed integrally with the syringe body.

10. The syringe as claimed in claim 9, wherein the syringe body is provided with a rib on the outer wall of the syringe body, the cap being removed from the syringe by forcing the cap against the abutment which causes rupture of the at least one frangible portion.

11. The syringe as claimed in claim 1, wherein the outer end of the needle holder contains a peripheral lip (37) that extends over a front face of the syringe body to hold the needle holder in position.

12. The syringe as claimed in claim 1, wherein the inner end of the needle holder comprises a plurality of fingers (75) which are spaced apart from each other, the spacing defining a recess (40), the fingers (75) able to be pushed together.

* * * * *